United States Patent
Hollis

[19]

[11] Patent Number: 6,081,741
[45] Date of Patent: Jun. 27, 2000

[54] INFRARED SURGICAL SITE LOCATING DEVICE AND METHOD

[75] Inventor: J. Marcus Hollis, Milton, Fla.

[73] Assignee: Vector Medical, Inc., Milton, Fla.

[21] Appl. No.: 09/314,101

[22] Filed: May 19, 1999

Related U.S. Application Data

[60] Provisional application No. 60/088,182, Jun. 5, 1998.

[51] Int. Cl.[7] .................................................. A61B 5/05
[52] U.S. Cl. .............................. 600/424; 600/473; 606/96
[58] Field of Search ...................................... 600/424, 476, 600/478, 473, 310, 160, 178, 182; 606/96

[56] References Cited

U.S. PATENT DOCUMENTS

| | | | |
|---|---|---|---|
| 4,444,185 | 4/1984 | Shugar | 128/305.3 |
| 4,621,628 | 11/1986 | Brudermann | 128/92 VD |
| 4,898,175 | 2/1990 | Noguchi | 128/634 |
| 5,423,321 | 6/1995 | Fontenot | 128/664 |
| 5,540,691 | 7/1996 | Eistrom et al. | 606/64 |
| 5,879,306 | 3/1999 | Fontenot et al. | 600/473 |
| 5,902,247 | 5/1999 | Coe et al. | 600/476 |
| 5,906,579 | 5/1999 | Vander Salm et al. | 600/424 |

Primary Examiner—Brian L. Casler
Attorney, Agent, or Firm—Jim Zegeer

[57] ABSTRACT

An apparatus and method for guiding a surgical instrument within and around the human body. During surgery on the body it is often necessary to approach a specific anatomical location precisely and directly in order to minimize unwanted surgical trauma and to place a soft tissue incision or a bone drill hole in an accurate location. The invention employs a light emitter an array of light sensors and a display to accurately locate an anatomical feature into which the light emitter has been placed. The light emitted from the emitter is detected after passing through a thickness of bone and/or soft tissue by the sensor array. The signal from the sensor array is processed and information indicating the relative direction of the emitter from the sensor is displayed. The surgeon then can proceed in the direction indicated. The system can be used for surgical aiming, locating and guidance to direct cutting, vascular surgeries or various types of visceral surgeries or brain surgery where the emitter catheter is guided into an area where surgery is performed. Other applications would not necessitate advancing through tissue but would be used for locating the position on the surface of a body overlying the emitter. An example of this would be to aim a radiation beam for cancer treatment. The sensor may be placed around a drill guide and the directional indicators used in orthopaedic surgery to locate an emitter placed within an intramedullary rod.

10 Claims, 7 Drawing Sheets

INFRARED SURGICAL SITE LOCATING DEVICE AND METHOD

This invention is the subject of provisional application Ser. No. 60/088,182 filed Jun. 5, 1998 entitled INFRARED (IF) SURGICAL SITE LOCATING DEVICE AND METHOD.

The present invention relates to the field of surgery, in particular to the guidance of surgical tools and locating anatomical features with a light emitter, an array of sensors and a direction display.

BACKGROUND OF THE INVENTION

During surgery it is necessary to locate a particular anatomic structure. This is often done by creating an incision through the skin and directly observing the structure. In some situations it is possible to advance a small tube or catheter into the structure of interest from a remote location such as through a vessel, cavity, or duct.

Light-emitting catheters have been used to produce an area of illumination on the surface of the body in order to locate a specific anatomical area. For example, U.S. Pat. No. 4,444,185 permits a tracheotomy by providing a device placed into a tracheal tube which emits outwardly directly light through the trachea and surrounding soft tissue as a means of locating the trachea. Also, in U.S. Pat. No. 5,540,691, a method and device are described for locating a hole in an intramedullary rod inserted into a long bone by observing illumination on the surface of the body provided by a light emitter place d within the intramedullary rod. U.S. Pat. No. 4,898,175 provides a method of observing images produced by light passed through body tissue to the surface. U.S. Pat. No. 5,423,321 presents a device a method for avoiding internal organs by placing a catheter which emits light along its length within the organ and placing a light sensor on the surgical tool and a means to indicate when light from the emitter is detected indicating proximity to the organ to be avoided.

However, none of the references cited above employ an array of sensors to precisely and accurately determine the direction of the emitter with respect to the sensor or to confirm precise and accurate centering over the emitter at low cost.

U.S. Pat. No. 5,423,321, "Detection of Anatomical Passages Using Infrared Emitting Catheter," is a method for determining proximity to anatomical structure by placing a single emitter or line or line of emitters in structure and determining proximity to surgical instrument by measuring intensity of light emitted. U.S. Pat. No. 5,423,321 merely teaches the use of a single light sensor to serve as an indicating of the proximity of the emitter. It does not provide or suggest precise and accurate information on the direction of the emitter from the surgical tool. It does not have an array of sensors or emitters. It does not give direction of source from the emitter.

The present invention provides precise and accurate information of the direction of emitter from sensor and indicates the precise center of the emitter and the direction of relative movement between the sensor array and emitter for precise and accurate positioning and orientation or alignment purposes. Thus, the invention can find an anatomical position and orientation for a surgical procedure much faster and easier.

U.S. Pat. No. 5,540,691, "Optical Distal Targeting Method for an Intramedullary Nail," is an apparatus for detecting the location of transverse holes of an intramedullary nail and aligning a drill with the holes. This system consists of a light source which is passed down the center of the intramedullary rod and a video system which is sensitive to infrared light which captures an image of the light transmitted through the transverse hole in the rod. The light simply shines out toward the surgeon who attempts to line up the drill by centering it on an area of light coming out of the hole. The infrared is visualized using either a video system sensitive to IR light or goggles which are sensitive to infrared. U.S. Pat. No. 5,540,691 requires the surgeon to wear night vision goggles or employ a video device which displays an image on a screen which shows the light transmitted through the tissue. There is no mechanism for automatically finding when the drill is accurately centered or oriented. The surgeon would need to divert his eyes to the video screen to judge when the light intensity was centered around the drill. Therefore, this system is much more difficult to use than the device of this invention. It would be much more difficult to accurately determine the center of a hole using the video system. The system and method of the invention is also much simpler and cheaper since one would not have to use a video system.

By using an array of inexpensive sensor elements, the center of the emitter can be quickly and precisely located with a minimum of trial and error, and then for alignment purposes, it provides the relative direction and relative amount of movement to rapidly achieve accurate alignment or orientation.

Thus, the object of the invention is to provide an infrared surgical site locating device and method which are accurate and precise, easy to use and low in cost.

DESCRIPTION OF THE DRAWINGS

The above and other objects, advantages and features of the invention will become more clear when considered with the following specification and accompanying drawings, wherein.

DETAILED DESCRIPTION OF THE INVENTION

Figure 1:
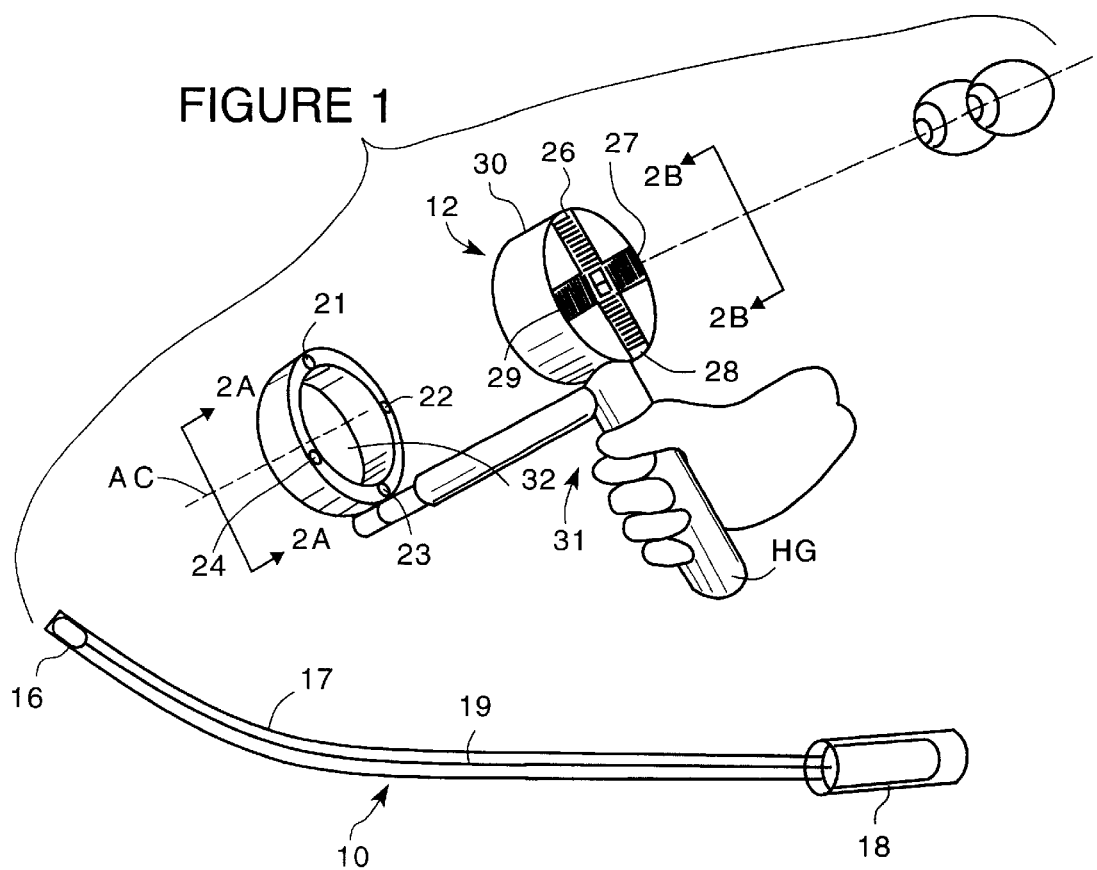
FIG. 1 is an isometric perspective view of the IR emitter or sender unit and the integrated sensor array and simplified display.
Figure 2A:
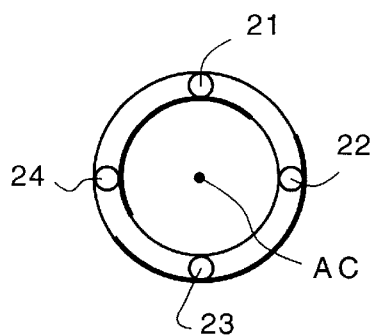
FIG. 2A is a view of the sensor array looking in the direction of the arrow AA in FIG. 1.
Figure 2B:
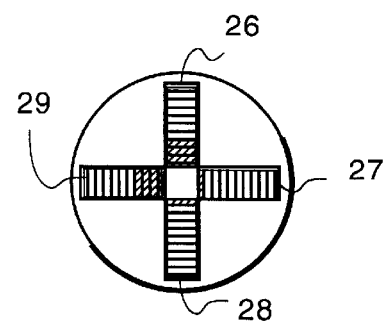
FIG. 2B is a view of the display looking in the direction of arrow BB in FIG. 1.

Referring to FIG. 1, the invention includes the following elements: emitter element 10, sensor array 11 and display element 12. These elements are described in greater detail.

Emitter assembly 10

Figure 10:
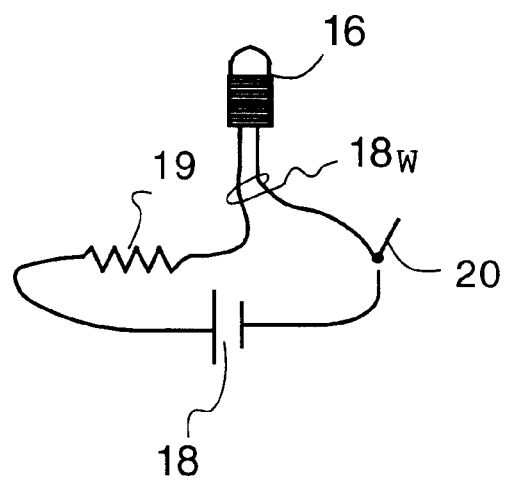
FIG. 10 is a circuit diagram of the emitter.

Emitter assembly 10 includes a light-emitting diode (LED) 16 contained within a bio-compatible plastic tube 17 and connected to a battery 18 at the other end of the tube by electrical wires 18W. (see FIG. 10). Preferably, the plastic tube 17 is sealed at both ends. The electrical current may be interrupted from the LED by displacing the battery from the battery holder through the wall of the tube or by a switch 20 (FIG. 10).

Sensor array 11

The sensor array assembly 11 comprises an array of infrared light sensors 21, 22, 23, 24 (numbering at least three and preferably four) and a means of displaying the intensity of light which strikes the light sensors. The axial center AC of the sensors 21, 22, 23, 24 may be axially aligned with the axial center of display 12. A means of preconditioning the electrical signal from the light sensors may also be provided (see FIGS. 8 and 11).

Display element 12

The display element 12 is so arranged that the direction of the higher intensity light is clearly indicated. In one preferred embodiment, this is accomplished by having multiple signal indicators 26, 27, 28, 29, one for each sensor 21, 22, 23, 24 in the sensor array, the signal indicators 26, 27, 28, 29 being carried in a frame 30 and arranged in the display in such a way that mimics the relative location of the sensors in the sensor array thereby indicating the direction of relative movement between the sensor array 11 and emitter 10 to achieve accurate orientation and alignment of the center of the sensor array.

In one form of the invention, the array of light sensors 11 is contained within a handled assembly 31 which has a port 32 for surgical tool access in the axial center AC of the array 11 and a handle grip HG as shown in FIG. 1. In this form of the invention, the access port 32 can be used with a cutting tool, such as a surgical drill (FIG. 3), to advance a surgical approach towards the emitter.

Figure 4:
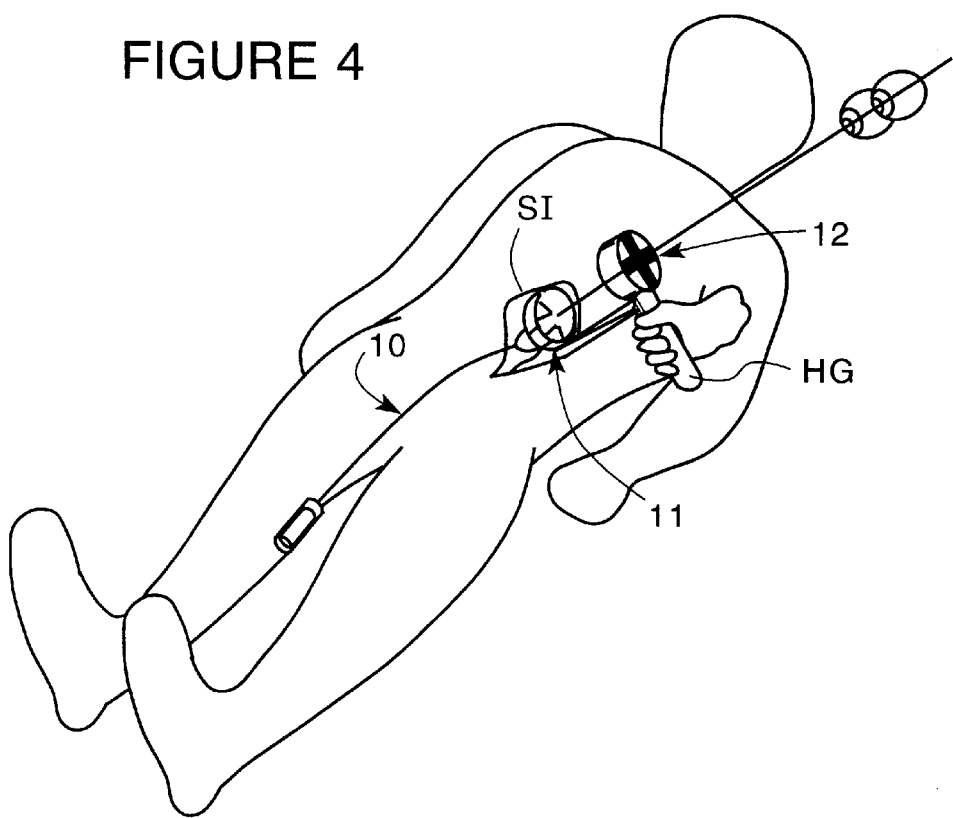
FIG. 4 is a diagrammatic illustration of the use of the invention for visceral surgery.

When used in visceral surgery, the invention can be used as illustrated in FIG. 4. The emitter element 10 would be passed from a remote relatively easily accessible site through a visceral passage to a location where surgery was indicated. The sensor array is then placed over the body and the light emitted by the emitter is detected and located. The sensor array is then centered over the light using the display means as a guide and a surgical incision is made through the access port. The sensor is then advanced towards the emitter along with the surgical approach until the visceral structure with the emitter is exposed. The sensor array is then removed and the surgery completed in the normal fashion by the skilled surgeon.

In another embodiment the invention is used for vascular surgery for locating vessels. The emitter element is passed through the vascular system from a remote, relatively easily assessable site such as a femoral artery to a site at which surgery is indicated. The sensor array is then placed over the body and the light emitted by the emitter is detected and located. The sensor array is then centered over the light using the display means as a guide and a surgical incision is made through the access port. The sensor is then advanced towards the emitter along with the surgical approach until the vessel containing the emitter is exposed. The sensor array is then removed and the surgery completed in the normal fashion by the skilled surgeon.

Figure 5:
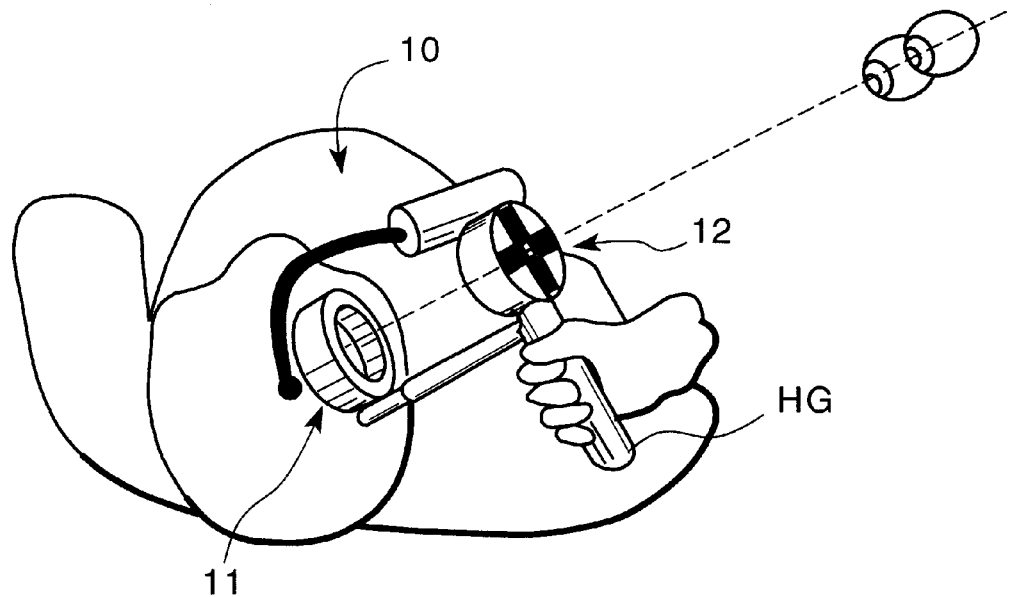
FIG. 5 is a diagrammatic illustration of the use of the invention for brain surgery, FIGS. 6 and 7A–7F taken together illustrate the principles of operation of the invention.
Figure 6:
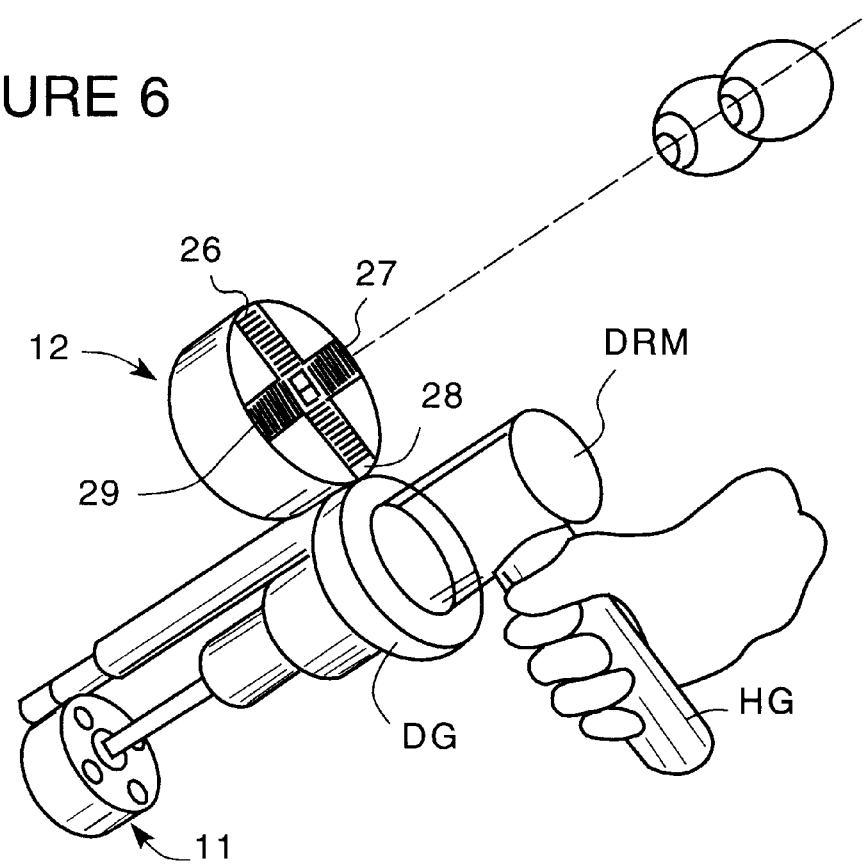

When used in cranial or brain surgery the invention would be used as illustrated in FIG. 5. The emitter element would be passed using the techniques of catheter procedures which are known in the art of medicine to a location where surgery was indicated. The sensor array would then be placed over the cranium and the light emitted by the emitter is detected and located. The sensor array is then centered over the light using the display means as a guide and the location of the sensor array noted. A surgical incision is then made down to bone. The sensor array, centered around a drill guide and drill would then be moved on the bone and centered over the light emitter using the display means as a guide. The drill would then be advanced and a hole formed in the bone. The drill and drill guide would then be removed from the sensor array. A surgical approach would then be advanced using the sensor array and display means to guide the direction of advancement until the anatomical structure of interest is reached. The sensor array is then removed and the surgery completed in the normal fashion by the skilled surgeon.

In a further utilization of the invention, the access port may be used to mark the surface of the body to allow for radiation therapy to be directed towards a structure containing the emitter. In this case, a location identified as being a target for radiation therapy would be identified using the techniques which are known in the art of medicine. The emitter element 10 would then be placed into the target location using the techniques of catheter procedures which are well known in the art of medicine. The sensor array 11 is then placed over the body and the light emitted by the emitter 10 is detected and located. The sensor array is then centered over the light using direction information presented in the display 12 as a guide. Using the access port centered within the sensor array 11, markings are placed on the skin identifying the area over the light emitter. Similarly, the area over the emitter can be located on the other side of the body forming a known trajectory along which the emitter would be known to lie.

Figure 3:
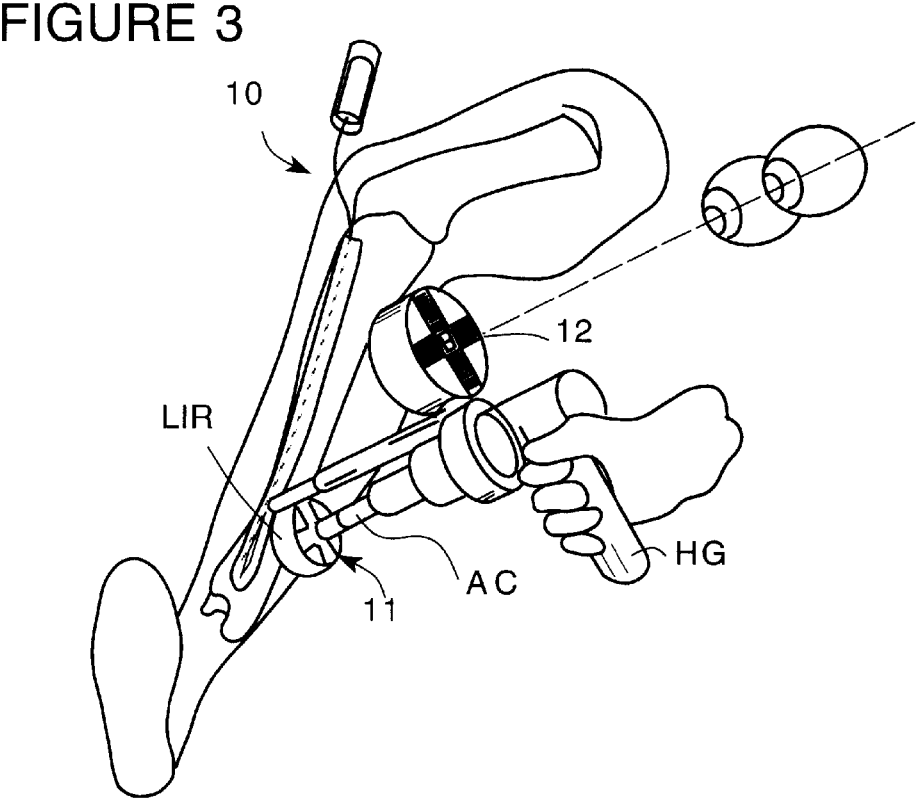
FIG. 3 is a diagrammatic illustration of use of the invention for accurate orientation of a surgical drill.
Figure 8:
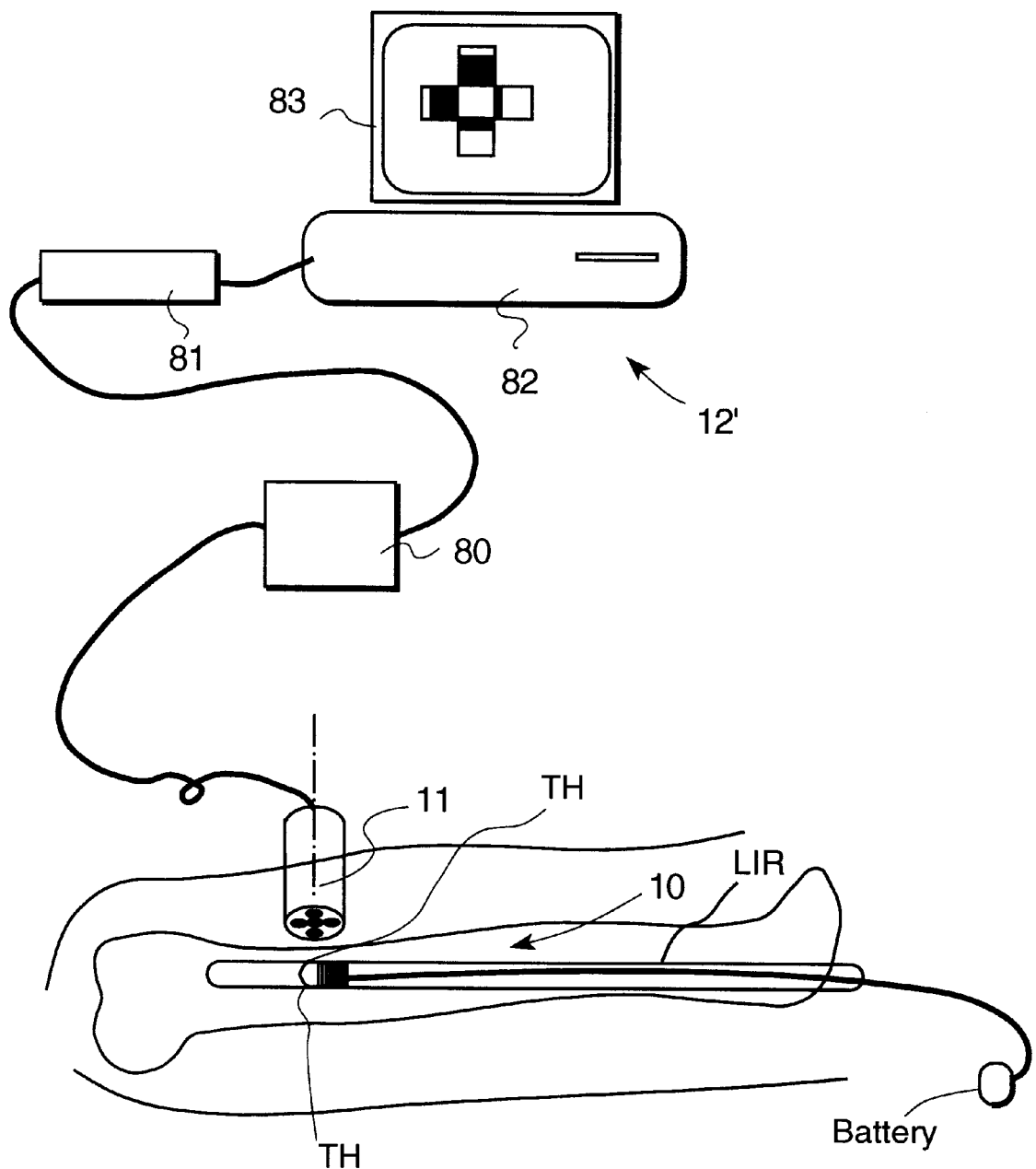
FIG. 8 is a block diagram of the invention circuitry.

In another form of the invention, the sensor and display assembly can be fixed to a surgical drill and the drill bit passed through a drill guide fixed within the access port centered in the sensor array (FIG. 3). In this embodiment the invention can be used for locating a drill hole for a locking screw in a long bone intramedullary rod LIR. The method for locating one or more intramedullary rod locking screw holes TH is illustrated in FIG. 8. The steps consist of: Placing the IF emitter element 10 within the center cannulation of the intramedullary rod LIR such that the light-emitting diode (LED) 16 is at the level of the transverse hole TH such that the light will shine through the hole TH. The rod is then inserted into the long bone in the normal fashion by the skilled surgeon The sensor array 11, fixed around a drill guide DG and drill, is then moved along the surface of the skin until the light from the emitter is detected and located. The sensor array 11 is then centered over the IR light from emitter 10 using the direction shown in the display 12 as a guide. The location of the sensor array 11 is then noted and a surgical incision is made and the surgical approach opened down to the long bone. The sensor array 11 is then placed on the surface of the bone. The sensor array 11 is then centered over the light using the display means 12 as a guide. At this point the surgical drill SG which is contained within the drill guide DG, centered in the sensor array, is centered over the LED 16 and thus the transverse hole TH in the intramedullary rod. The drill SG is then powered and advanced through the cortex of the bone. The IR emitter 10 is then retracted away from this transverse hole TH in the intramedullary rod and the drill is advanced through the rod into the cortex on the far side of the long bone. If additional holes are to be drilled, the LED 16 is retracted a position corresponding to the additional transverse holes using markings on the tube to gauge the proper depth. The process is then repeated through the same incision or through additional incisions depending on the judgment of the skilled surgeon.

Principle of Operation

It has been well established that light, especially in the red and infrared spectrum can pass through biological tissue. As with any radiant energy, the intensity of the energy at any point is lessened as the distance from a point source is increased. This is caused both by the spreading out of the energy over a wider area as you move away from the source but also, as in the case of light through tissue, adsorption of the energy by the medium. The present invention uses these phenomena in a novel way to solve a persistent problem in surgery which is to precisely locate anatomical structures and locations through overlying tissue. This is done by providing an array of sensors 11, preferably four, in order to detect the gradient of light intensity, and the symmetry of that energy within the sensor array 11. The novel method for the layout and design of the sensors and display provide for a reproducible, precise, quick, intuitive, and easily learned way to locate the center of a field of light emanating from a point source and at low cost.

Figure 7A:
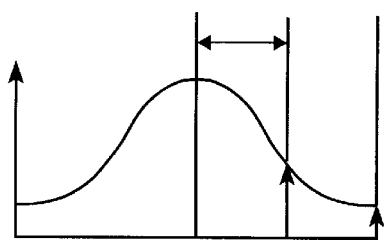
Figure 7B:
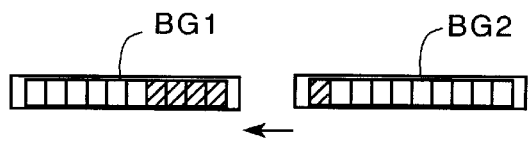
Figure 7C:
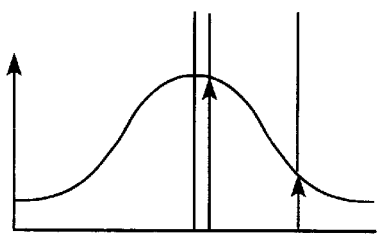
Figure 7D:
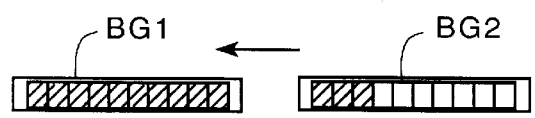
Figure 7E:
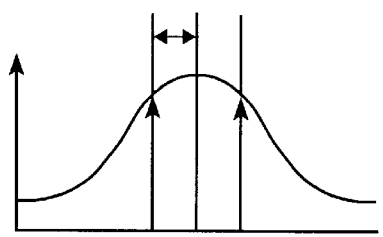
Figure 7F:

FIG. 7A is a plot of light intensity vs. position on a cross-section through the tissue above the location of a light emitter 10. It can be seen that the light intensity falls off quickly away from the center area of the plot representing the point over the light source. Also shown in FIG. 7A are lines showing the location of two light sensors. FIG. 7B is a display of two inexpensive LED bar graphs BG1, BG which, in the preferred embodiment would be a linear array of LED's. These LED bar graphs are connected to electronic circuitry designed to illuminate the LED's in sequence for increasing light intensity falling on the light sensor corresponding to that indicator. Thus, the LED bar graph is an indicator of the light intensity at one sensor and two together give an indication of direction of movement that may be required to accurately center the array 11 on the IR light emitter 10. The electronic circuit may have a variable sensitivity adjustment if desired. It can be seen when looking at the sensor location in FIG. 7A that the sensors are not centered over the emitter. The light intensity at the location of the sensors is therefore not equal between the two sensors. This is indicated by the unequal number of LED's in the bar graphs illuminated in the two LED bar graphs in FIG. 7B. The operator of the invention would move the sensor array in the direction of the sensor with the highest light intensity. Shown in FIG. 7C, the sensors have moved in the direction of the center of the light source. The light intensity, however, is still uneven as indicated by the LED bar graphs in FIG. 7D. FIG. 7E shows the sensors centered over the light source. The light intensity is equal in each sensor as demonstrated by the LED bar graphs in FIG. 7F. The same technique is used when approaching the center from the other direction. The sensor is moved in the direction of the higher intensity light striking the sensor. This technique will work whether the center of the light emitter is within the sensor array or outside of the sensors. For two dimensional centering, an additional pair of sensors and bar graphs are added perpendicular to the first. These work in the same way to provide alignment along the other axis.

In FIG. 8, instead of individual bar graphs associated with each sensor, the analog sensor signals from the sensor circuitry 80 is fed via analog-to-digital converter 81 to computer 82 which outputs to monitor 83 an image corresponding, in this embodiment, to the bar graph display. The display could simply be arrows indicating direction and the length of the arrow indicating the relative amplitude or distance to achieve alignment.

Figure 9:
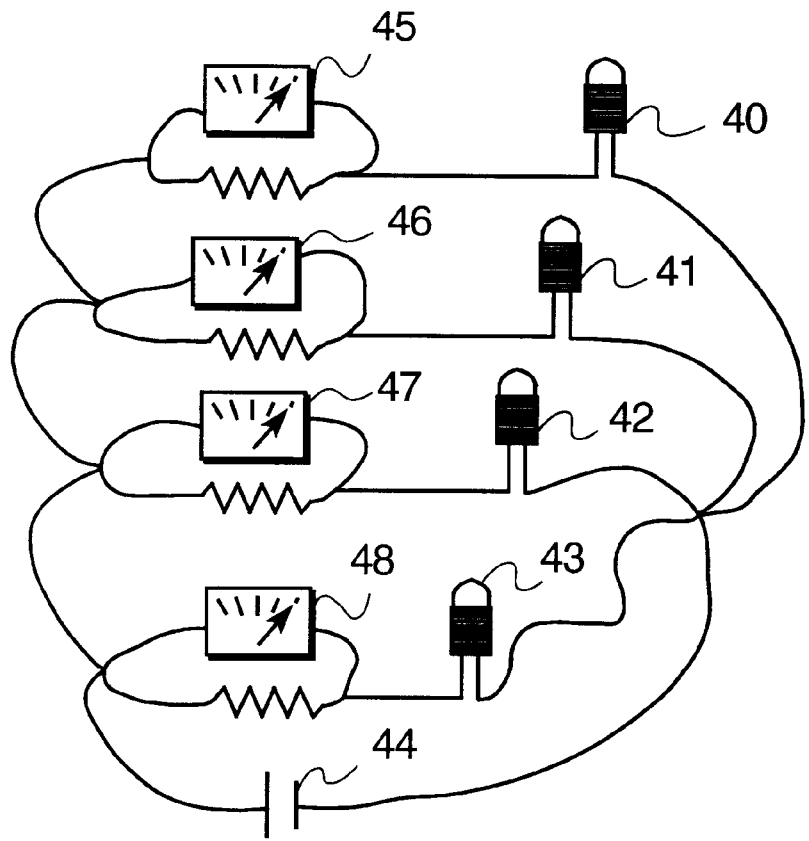
FIG. 9 illustrates one embodiment of the invention wherein voltmeters are used as a display or output mechanism.

In FIG. 9, instead of bar graphs, IF photoresistors 40, 41, 42 and 43 are in circuit with a battery 44 and a resistor voltmeter combination 45, 46, 47 and 48. In this embodiment, the voltmeter serves the same function as the bar graphs.

Figure 11:
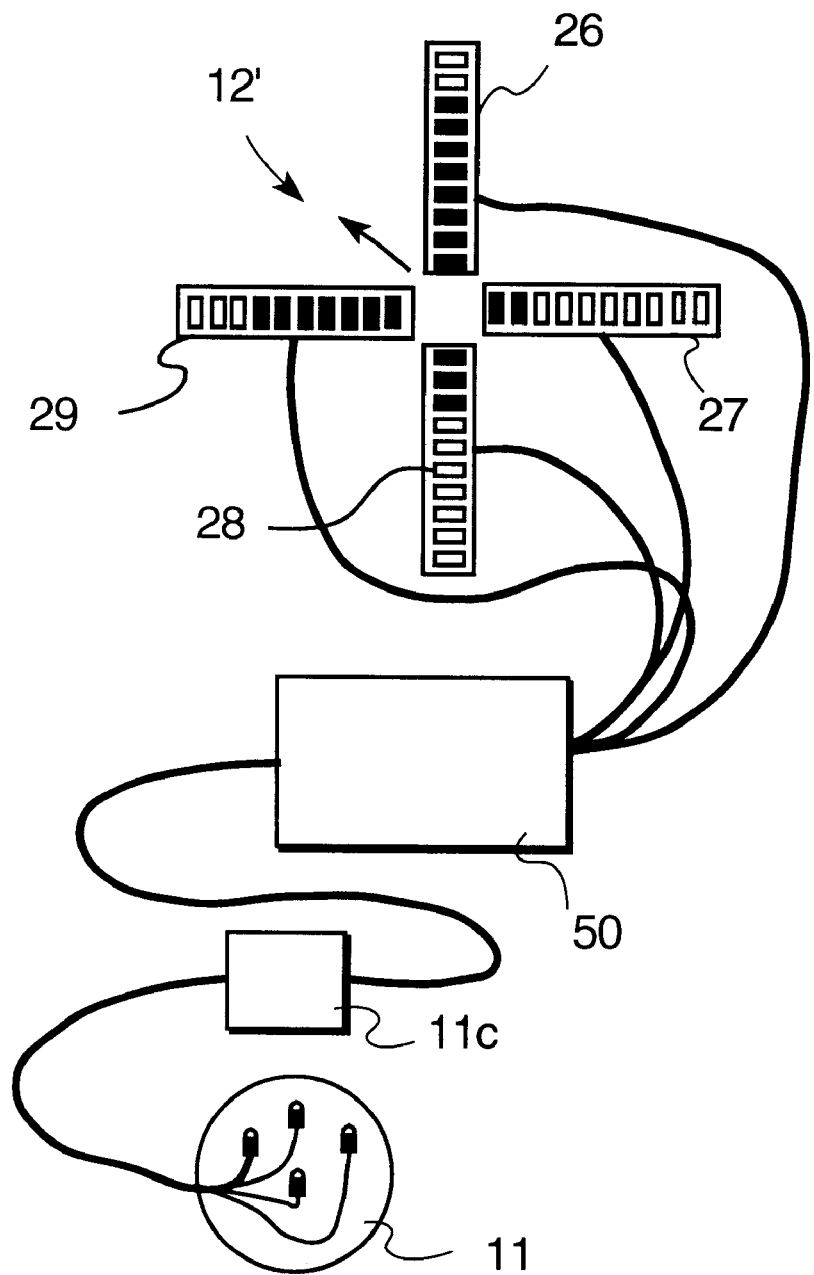
FIG. 11 is a block diagram of the invention using an LED display.

In FIG. 11, the sensor array 11 and its circuitry 11C is coupled to the bar graph emitter BG in display 12' by a single board computer or digital processor 50 (which includes an analog-to-digital converter) which, in turn supplies data to bar graph display 11'.

The invention therefore provides a simple and accurate means for indicating the direction of the emitter relative to the sensor array and indicating clearly when the sensor array is centered over the emitter. This enables surgeons to locate anatomical structures containing the emitter much faster and simpler than has previously been possible.

While the invention has been described in relation to preferred embodiments of the invention, it will be appreciated that other embodiments, adaptations and modifications of the invention will be apparent to those skilled in the art.

What is claimed is:

1. A guidance system for locating points in a living body having passages therein comprising:
   a. an emitter for emitting light of a predetermined frequency and means for introducing said emitter into a selected passage in said living body,
   b. a detector having a plurality of individual sensors mounted in a sensor array such that light from said emitter passing through tissue in said living body impinges on one or more sensors of said sensor array and produces an electrical signal proportional to the light impinging thereon,
   c. a processor for processing intensity of light from said light emitter passing through said body tissue and falling on each sensor, respectively, in said sensor array, and
   d. an indicator display connected to said processor for indicating the relative intensity of light impinging on said sensors, respectively, as a function of a location of said light emitter in said living body.

2. The guidance system defined in claim 1 wherein said predetermined frequency is infrared.

3. The guidance system defined in claim 1 wherein said means for introducing includes a catheter.

4. The guidance system defined in claim 1 wherein said means for introducing is adapted to position said emitter at the target zone for radiation treatment.

5. In a bone drill guide for guiding a drill bit to specific point for drilling a hole in bone having an intramedullar canal, comprising a guidance system for locating a point in said bone including:
   a. an emitter for emitting infrared light and means for introducing said emitter into said intramedullar canal,
   b. a detector having a plurality of individual sensors mounted in a sensor array adapted to surround said drill bit such that light from said emitter passing through tissue in said living body impinges on one or more sensors of said sensor array and produces an electrical signal proportional to the light impinging thereon,
   c. a processor for processing intensity of light from said light emitter passing through bone tissue and falling on each sensor, respectively, in said sensor array, and
   d. an indicator display connected to said processor for indicating the relative intensity of light impinging on said sensors, respectively, as a function said specific point and location of said light emitter in said bone tissue for guiding said drill bit.

6. The bone drill guide defined in claim 5 wherein said means for introducing includes a hollow infrared opaque hollow rod having one or more apertures therein for passing infrared light from said emitter through bone to said sensors.

7. A guidance system for locating a point in a living body having passages therein comprising:

a. emitter for emitting light of a predetermined frequency and means for introducing said emitter into a selected passage in said living body, b. a detector having a sensor array constituted by at least three individual sensors mounted in an array such that light from said emitter passing through tissue in said living body impinges on one or more sensors in said sensor array, c. a processor connected to said sensor array for determining the location of the emitter and said point relative to the sensor array, and d. an indicator connected to said processor for indication of direction of emitter relative to said sensor array to precisely locate said point.

8. The guidance system defined in claim 7 wherein said means for introducing includes a hollow rod.

9. The guidance system defined in claim 7 wherein said means for introducing includes a catheter.

10. A surgical guidance method for locating a point in a living body having passages therein comprising the steps of:

a. introducing an emitting infrared light emitter into a selected passage in said living body, b. providing a detector having a plurality of individual infrared light intensity sensors mounted in a predetermined pattern and detecting light from said emitter passing through tissue in said living body which impinges on one or more sensors in said sensors in said predetermined pattern, and c. displaying a relative light intensity of light detected by each sensor in said predetermined pattern in such a manner to provide an accurate indication of a relative direction of movement to achieve alignment and orientation.

* * * * *